United States Patent
Beyerlein et al.

(10) Patent No.: US 7,899,150 B2
(45) Date of Patent: Mar. 1, 2011

(54) COMPUTED TOMOGRAPHY DEVICE INCLUDING TRANSMITTERS FOR CONTACTLESS TRANSMISSION OF DATA AND ELECTRICAL POWER

(75) Inventors: Walter Beyerlein, Bubenreuth (DE); Werner Kühnel, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 249 days.

(21) Appl. No.: 11/665,792

(22) PCT Filed: Oct. 18, 2005

(86) PCT No.: PCT/EP2005/055342
§ 371 (c)(1),
(2), (4) Date: Nov. 24, 2008

(87) PCT Pub. No.: WO2006/076971
PCT Pub. Date: Jul. 27, 2006

(65) Prior Publication Data
US 2009/0304144 A1 Dec. 10, 2009

(30) Foreign Application Priority Data
Oct. 20, 2004 (DE) .......................... 10 2004 051 170

(51) Int. Cl.
*H05G 1/10* (2006.01)
*H05G 1/08* (2006.01)
(52) U.S. Cl. .............................. 378/15; 378/91; 378/101
(58) Field of Classification Search .................... 378/15, 378/91, 101, 102, 197
See application file for complete search history.

(56) References Cited

U.S. PATENT DOCUMENTS

| | | | |
|---|---|---|---|
| 4,225,851 A | | 9/1980 | Reschovsky et al. |
| 4,259,584 A | * | 3/1981 | Krumme .......................... 378/15 |
| 4,323,781 A | | 4/1982 | Baumann et al. |
| 4,912,735 A | | 3/1990 | Beer |
| 5,018,174 A | * | 5/1991 | Collins .............................. 378/4 |
| 5,046,003 A | * | 9/1991 | Crawford ......................... 378/15 |
| 5,055,821 A | * | 10/1991 | Keller et al. ............. 340/286.01 |
| 5,608,771 A | | 3/1997 | Steigerwald et al. |

(Continued)

FOREIGN PATENT DOCUMENTS

DE 41 36 030 A1 5/1992

(Continued)

OTHER PUBLICATIONS

German Office Action for DE 10 2004 051 170.5-35 dated Aug. 3, 2005 and English translation.

(Continued)

*Primary Examiner* — Allen C. Ho
(74) *Attorney, Agent, or Firm* — Brinks Hofer Gilson & Lione (57) ABSTRACT

A computer tomography device is provided. The computer tomography device includes a rotating part and a stationary part. The rotating part has an X-ray tube for radiographing an object to be examined with X-rays and a detector for detecting the X-rays transmitted through the object. A stationary part has a data processing device for evaluating the detected measuring results, and a transmitter for supplying the X-ray tube and/or the detector and other rotating consumers with supply voltage by contactless transmission of electric power between the stationary and the rotating part. The transmitter is designed for contactless data transmission between the stationary part and the rotating part in addition to the contactless transmission of electrical power.

13 Claims, 6 Drawing Sheets

U.S. PATENT DOCUMENTS

| | | | |
|---|---|---|---|
| 6,301,324 B1 * | 10/2001 | Pearson et al. | 378/15 |
| 6,575,624 B2 * | 6/2003 | Noegel et al. | 378/198 |
| 6,674,836 B2 * | 1/2004 | Harada et al. | 378/107 |
| 7,054,411 B2 * | 5/2006 | Katcha et al. | 378/101 |
| 7,197,113 B1 * | 3/2007 | Katcha et al. | 378/101 |
| 7,425,096 B2 * | 9/2008 | Beyerlein et al. | 378/203 |
| 7,593,502 B2 * | 9/2009 | Katcha et al. | 378/4 |
| 7,613,273 B2 * | 11/2009 | Beyerlein et al. | 378/4 |
| 7,634,046 B2 * | 12/2009 | Krumme | 378/19 |
| 7,717,619 B2 * | 5/2010 | Katcha et al. | 378/197 |
| 2007/0035883 A1 * | 2/2007 | Katcha et al. | 360/281.8 |
| 2009/0060123 A1 * | 3/2009 | Nakayama et al. | 378/15 |
| 2009/0116618 A1 * | 5/2009 | Nakayama et al. | 378/107 |
| 2010/0066340 A1 * | 3/2010 | Delforge | 323/305 |

FOREIGN PATENT DOCUMENTS

| | | |
|---|---|---|
| DE | 197 00 110 A1 | 7/1998 |
| DE | 100 37 294 | 1/2002 |
| EP | 0 456 114 A2 | 11/1991 |
| EP | 0 564 292 A2 | 10/1993 |
| GB | 2 250 410 A | 11/1990 |

OTHER PUBLICATIONS

German Office Action for DE 10 2004 051.5-35 dated Aug. 3, 2010 and English translation.

* cited by examiner

COMPUTED TOMOGRAPHY DEVICE INCLUDING TRANSMITTERS FOR CONTACTLESS TRANSMISSION OF DATA AND ELECTRICAL POWER

The present patent document is a 35 U.S.C. §371 nationalization application of PCT Application Serial Number PCT/EP2005/055342 filed Oct. 18, 2005, designating the United States, which is hereby incorporated by reference, which claims the benefit pursuant to 35 U.S.C. §119(e) of German Patent Application No. 10 2004 051 170.5, filed Oct. 20, 2004, which is hereby incorporated by reference.

BACKGROUND

The present embodiments relate to a computed tomography ("CT") device having transformer-type transmitters for the contactless transmission of electric power in the sense of a transfer of energy from a stationary part to components of a rotating part.

X-ray CT is an x-ray recording method, which has a different image structure than the conventional x-ray layer recording method. In the case of CT recordings, transverse sectional images are obtained, such as images of body layers. The images of body layers are oriented perpendicular to the axis of the body. The tissue-specific physical variable shown in the image is the distribution of the attenuation value of x-ray radiation $\mu(x,y)$ in the sectional plane. The CT image is obtained by reconstructing the one-dimensional projections of the two-dimensional distribution of $\mu(x,y)$ provided by the measuring system used from numerous different viewing angles.

The projections originating from different directions, such as at a projection angle $\alpha$, are obtained using a combined x-ray tube-detector system. The x-ray tube-detector rotates in the plane of the layer about the object. The x-ray tube-detector may include "fan beam devices" having a tube and an array of detectors (a linear or partially circular arrangement of detectors) rotating in the plane of the layer in a common manner about a center of rotation. The center of rotation is also the center of the circular measurement field.

Figure 1:
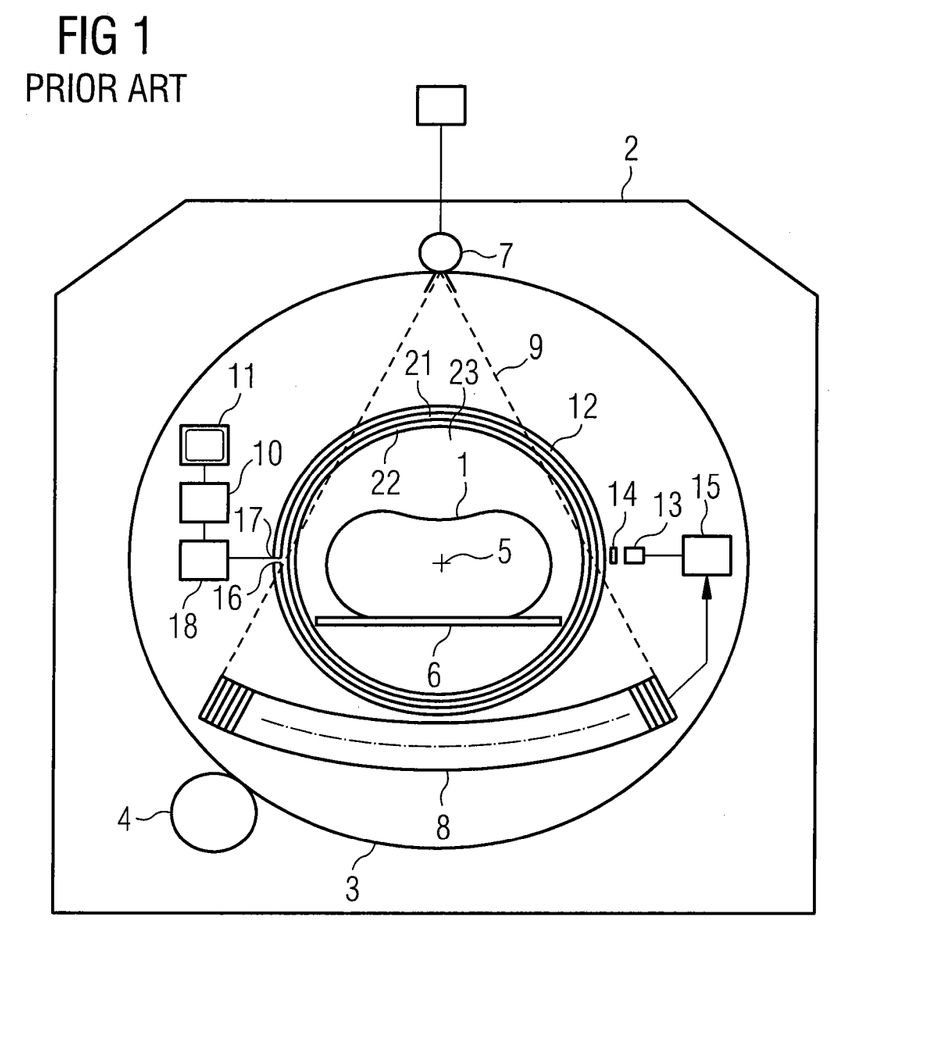
FIG. 1 shows a schematic diagram of a computed tomography device with contactless transfer of electric power and optical transfer of measurement data according to the prior art.

FIG. 1 shows a schematic diagram of a CT device for a fan beam method. The CT device comprises a rotatable support 3 in a frame 2. The rotatable support 3 is able to be rotated by a motor 4 about an axis 5 running perpendicular to the plane of the drawing.

An x-ray tube 7 and a detector 8 for x-ray radiation are provided to scan the patient 1 lying on a support 6. The x-ray tube 7 emits a fan-shaped x-ray radiation beam 9. The entire transverse layer of the patient 1 to be examined is penetrated by x-ray radiation beam 9. The thickness of the x-ray radiation beam 9 perpendicular to the plane of the layer is equal to the thickness of the layer, for example, a few millimeters.

In order to scan the patient 1, the measuring arrangement, which includes x-ray tube 7 and detector 8, is rotated 360° about the patient 1 and a set of output signals of the detector 8 is read at predetermined projections (e.g. $\Delta\alpha=1°$).

The detector 8 includes a series of single detectors, for example, 256 single detectors, so that $\alpha$, for example, 256, signals of the detector 8 are read (detected) per projection. For example, 360×256 signals are available for processing per scanning procedure. The signals are transmitted to a fixed (stationary) data processing facility. The data processing facility calculates the attenuation values $\mu(x,y)$ of predetermined points in the examined transverse layer of the patient 1 in the form of a matrix. The data processing facility effects a pixel-based image reproduction on a screen 11.

FIG. 1 shows an exemplary embodiment of a double contactless, inductive energy transmission from the stationary part to the x-ray tube 7 and to the detector 8 by transmitters 21, 22. The transmitters 21, 22 respectively form a transformer. The transmitters 21, 22 are configured as concentric rings and enclose the opening 23. The opening 23 receives the patient 1.

Figure 2A:
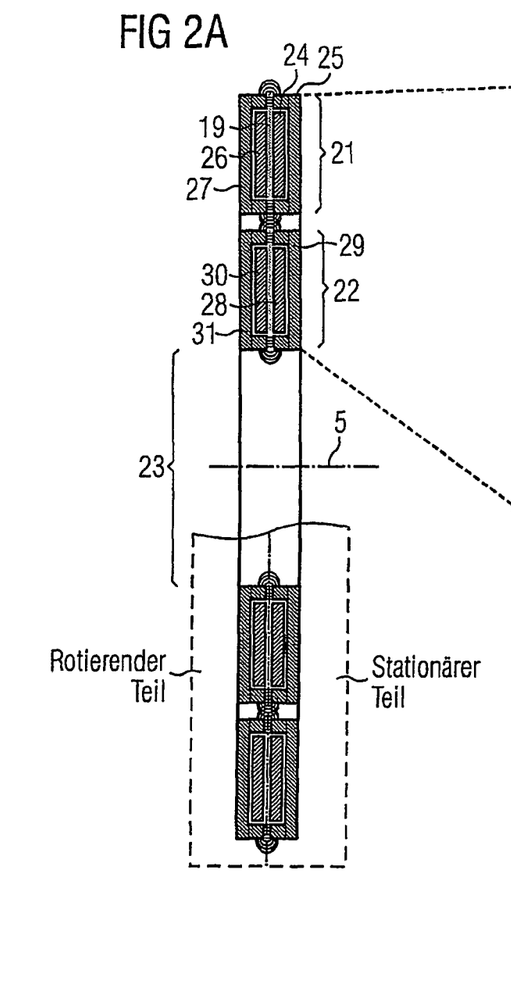
FIG. 2A is a cross section view of one embodiment of the transmitters used for the transfer of power.

FIG. 2a shows a cross section of the two annular transmitters 21, 22. Typically, each transmitter 21, 22 has a primary winding and a secondary winding, which are surrounded by a transmitter core.

The transmitter core of the outer transmitter 21 is a pot-type core enclosing the primary winding 24 and the secondary winding 26. The outer transmitter 21 includes two core parts 25, 27 of U-shaped cross section. The two core parts 25, 27 are oriented with their flange-type shoulders facing each other. The core part 27 and the secondary winding 26 of the first (outer) transmitter 21 or, respectively, the core part 31 and the secondary part 30 of the second (inner) transmitter 22 are fixed in relation to the rotatable support 3 and the x-ray tube 7 and detector 8, and rotate with the measuring arrangement 7, 8. The other core part 25 and the primary winding 24 of the outer transmitter 21 or, respectively, the other core part 29 and the primary winding 28 of the inner transmitter 22 are provided in a fixed manner in the device. An air gap 19 is left between the two core parts 25, 27 or, respectively, 29, 31.

The electric power required can be transmitted in an inductive and contactless manner to the rotating part of the gantry (scanning unit comprising x-ray source 7, detector 8 with electronic measuring system and mechanical structure, e.g. rotatable support 3). The power consumption of the x-rays tube at approx. 80 kWatt is significantly higher than the power consumption of all further components of the rotating part of the gantry (rotary anode, detector, electronic measuring system, heating unit for the x-ray tube, etc.), which is around 10 kWatt in total. The electrical supply is divided into two separate load circuits and use two separate transmitters 21, 22. Separation of the two supply units allows optimum design of both load circuits.

An inductive and contactless transmission of electric power does not use energy transmission by way of slip rings. The inductive and contactless transmission of electric power avoids, for example, sparking, loss of contact and premature wear. The transfer of measurement data uses a contactless transmission, for example, optically or by way of a high-frequency transmission system, with modern CT systems.

FIG. 1 shows an optical transmission system for contactless transmission of detector signals. A ring 12 is made of light-conducting material (e.g. plexiglass) and curved around the axis of rotation 5. The ring 12 is irradiated at one point by way of an optical system 14 using a light source 13. The light source 13 is connected to a modulation stage 15, which converts the detector signals to light signals. The ring 12 is configured in such a manner that the light from the light source 13 is routed over the entire ring 12 periphery. The ring 12 has a gap 16 and a light detector 17, which converts the light signals back to electrical signals. The light detector 17 is disposed on one of the faces bordering the gap 16. The light signals are demodulated in a demodulation stage 18 and are supplied to the data processing facility 10. Signal transmission takes place during a projection in a consecutive manner. The detector signals of the individual detector elements are transmitted consecutively by the described facility.

The light source 13 can, for example, be a luminescence or laser diode operating in the infrared range. The modulation stage 15, the light source 13, and the optical system 14 rotate with the rotating part of the gantry (x-ray tube 7, detector 8, etc.) while the patient 1 is being scanned. The ring 12, the light detector 17, the demodulation stage 18, and the data processing facility 10 with the screen 11 are stationary. Such an optical (data) transmission system is very complex and cost-intensive because of the large number and complexity of the components.

To summarize, an immense transfer of energy takes place between the stationary part and the rotating part of the gantry of a CT device. An intensive data exchange takes place, with both control signal data for process control and measurement data obtained using detectors and electronic measuring systems. While the transfer of the control signal data between the rotating and stationary parts takes place in a bi-directional manner, the measurement data for obtaining and processing the images has to be transmitted unilaterally to the stationary part. Conventionally, this data transfer took place by way of slip rings and/or on fiber-optical transmission paths.

SUMMARY

The present embodiments may obviate one or more of the drawbacks or limitations in the related art. For example, in one embodiment, a CT x-ray apparatus is provided without error-prone slip ring technology or, an extremely complex and cost-intensive optical transmission technology or high-frequency transmit transmission technology for the data transfer between the rotating and stationary parts of the gantry.

In one embodiment, a CT device includes a rotating part with an x-ray tube to irradiate an object to be examined with x-ray radiation and with a detector to detect the x-ray radiation transmitted through the object. The CT device also includes a stationary part with a data processing facility to evaluate the detected measurement results and a transmitter to supply voltage to the x-ray tube and/or the detector and other rotating consumers by a contactless transmission of electric power between the stationary and rotating parts. The transmitter is designed for a contactless data transmission between the stationary and rotating parts and the contactless transmission of electric power.

The contactless data transmission can take place in an inductive or capacitive manner.

In the case of a contactless inductive data transmission, inductances in the power circuit and coupling capacitances in the data transmission circuit are combined.

In the case of a contactless capacitive data transmission, data transmission takes place by a symmetrical coupling of the data signal into the power circuit by coupling capacitances and on the basis of a common reference potential in the return system.

Where two transmitters are used to supply voltage, the data signal is forwarded by the first transmitter and the data signal is returned by the second transmitter.

Where two transmitters are used, the screening rings may be disposed between the first and second transmitters.

The screening rings can be disposed in an overlapping arrangement. The screening rings can be disposed on the opening side and/or outside.

The screening rings are made of a material with good electrical conductivity.

DETAILED DESCRIPTION

The present embodiments relate to computed tomography devices with contactless transmission of electric power by one or more rotating transmitters. The present embodiments also relate to data transfers by way of the transmitter(s). Inductive transmission and capacitive transmission are possible options.

Figure 3:
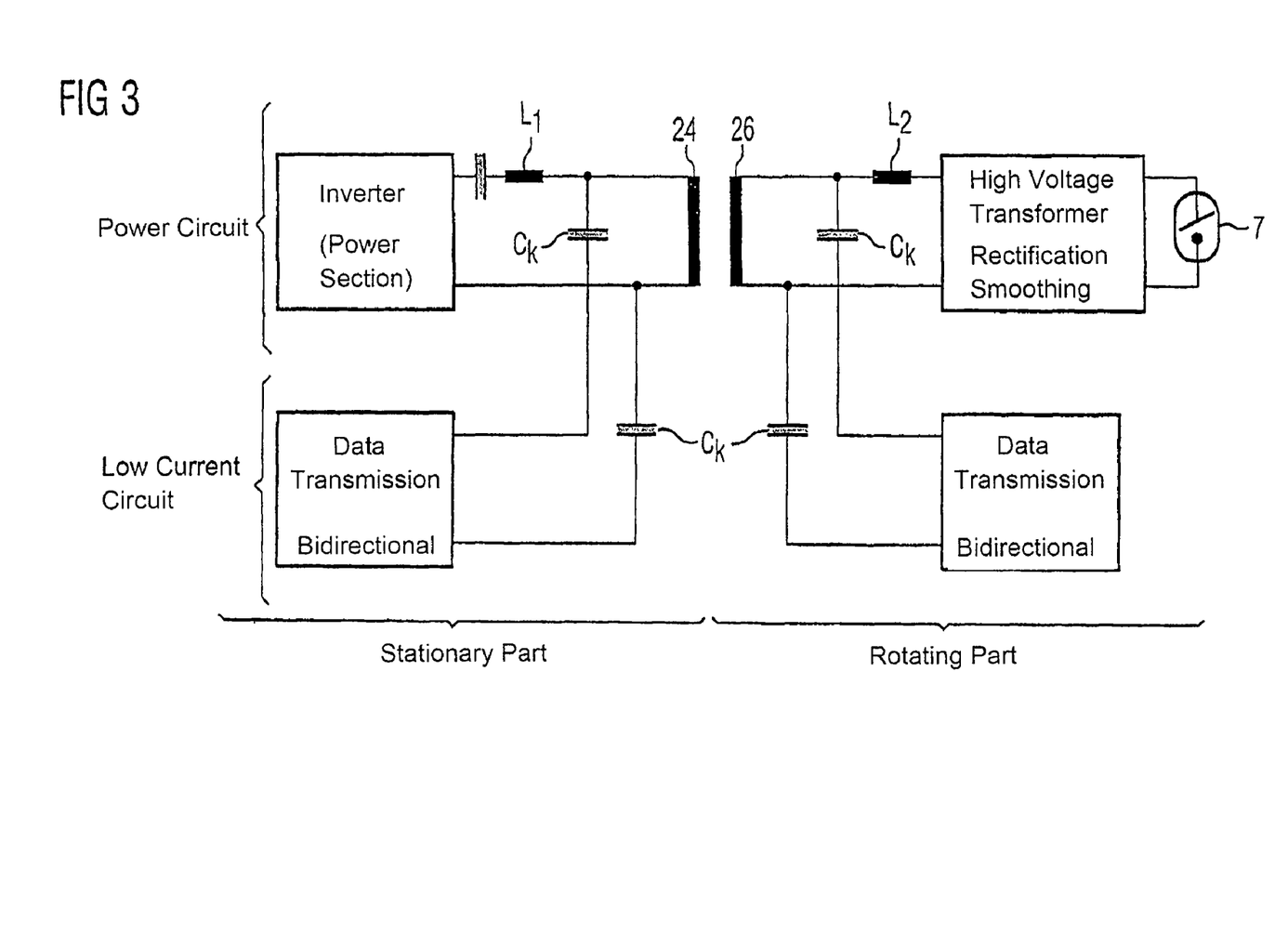
FIG. 3 shows one embodiment of an electric circuit for inductive contactless data transmission when using one transmitter for the contactless transfer of electric power in a CT device.

In one embodiment, as shown in FIG. 3, an electric circuit for inductive data transmission uses a single transmitter. The electric circuit is divided into a power-current circuit (load circuit upper half) for transmitting the high voltage to the rotating x-ray tube 7 and a light-current circuit (lower half) for the bi-directional transmission of data (signal, measurement and control data). As shown in FIG. 3, the data is injected into or extracted from the power-current circuit with low voltage by way of four coupling capacitors $C_K$.

The x-ray tube 7 is supplied, in the power-current circuit, by a high-voltage transformer by way of a high-voltage rectifier. Smoothing generally takes place by capacitors. The primary winding of the high-voltage transformer is connected to an inverter for high frequency on the order of 10 to 50 kHz, supplied by a rectifier. The input of the rectifier is connected to the rotating secondary winding 26 of the first transmitter 21 shown in FIG. 2A. The stationary primary winding 24 is supplied by an inverter for high frequency, connected to the supply network by way of a line rectifier. The x-ray tube 7 is supplied with up to 80 kW electric power in a contactless manner by way of the power-current circuit.

According to the present embodiments, the low-voltage data signals (control data signals, measurement data) are overlaid directly by the light-current circuit, shown in FIG. 3, by four coupling capacitors $C_K$ on the oscillation used for power transmission. Control signals that control the electronic measuring system, activate the x-ray tube, etc., are transmitted bi-directionally and measurement signals are transmitted unidirectionally from the rotating part to the stationary part. Depending on the electronic measuring and control systems, the power in the light-current circuit is 1 to 10 Watt. Like the power transfer according to FIG. 3, the data is transmitted solely in an inductive manner by way of the primary coil 24 and the secondary coil 26.

The data transmission is at least ten times greater than the oscillation frequency used for the power transmission in the power-current circuit. Since the oscillation frequency is around 50 kHz according to the prior art, the data transmission is at least 500 kHz to 1 MHz.

The oscillation used for the power transmission and the data signals are decoupled by the selected frequency interval through the inductances $L_1$, $L_2$ in the power circuit and through the coupling capacitances $C_K$, to the extent that these do not influence each other.

The (rotating) transmitter is dimensioned according to power transmission requirements. The (rotating) transmitter is optimized for approx. 50 kHz and approx. 80 kWatt. Initially, the data transmission is not taken into account. This means that the load circuit, designed to be extremely low-resistance due to the high power, dampens the high-frequency data signal, in such a manner that higher voltage levels than normal have to be used for clean transmission of the data signal.

Figure 4:
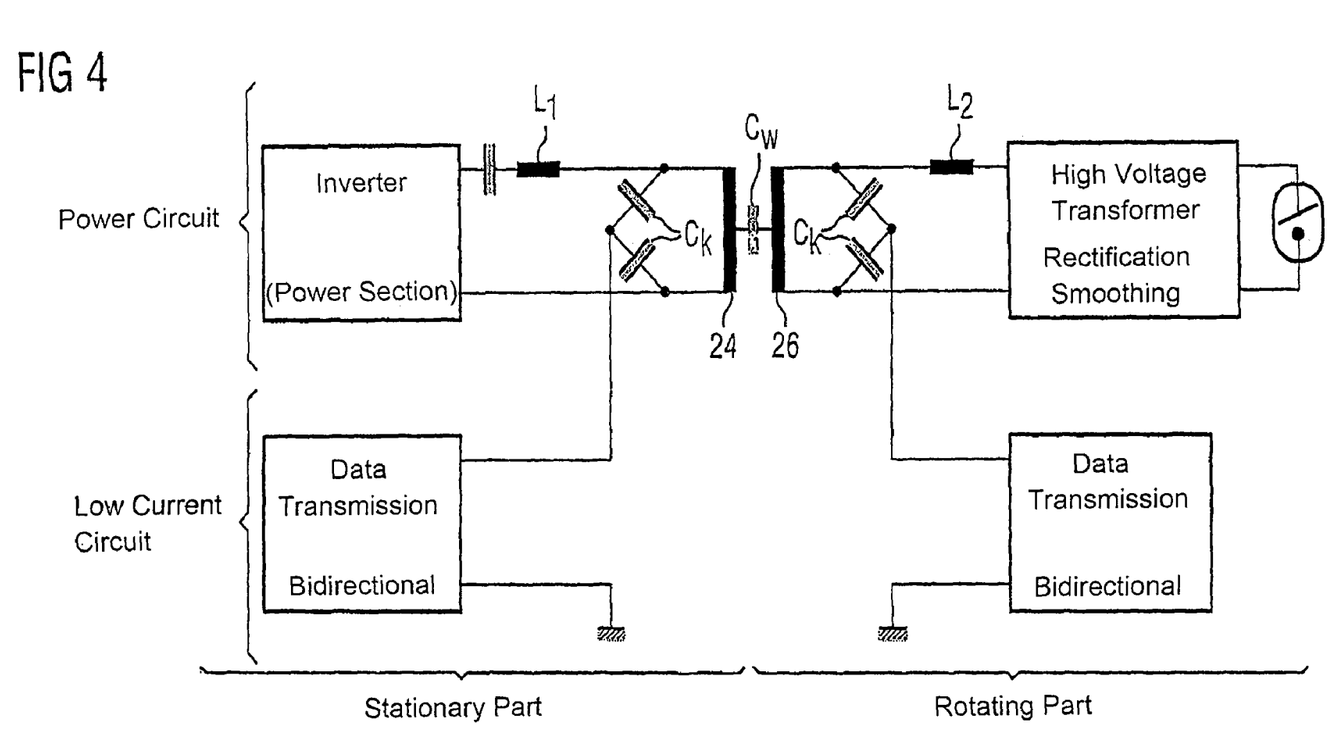
FIG. 4 shows one embodiment of an electric circuit for capacitive contactless data transmission when using one transmitter for the contactless transfer of electric power in a CT device.

In one embodiment, as shown in FIG. 4, the data transfer is represented by a capacitive transmission.

The upper part of FIG. 4 shows a power-current circuit, similar to the one in FIG. 3. The data signals of the light-current circuit are symmetrically coupled to the transformer windings 24, 26. There is no additional current flow and no change in induction in the primary coil 24 and in the secondary coil 26. The symmetry of this bridge-type coupling results in bilateral compensation. The respective data signal only brings about a change in the winding capacitance $C_W$ between the transformer windings. Magnetic transmission is prevented. The winding capacitance $C_W$ is shown with a broken line. The winding capacitance $C_W$ results from the physical nature of the transformer and is not a separate component.

As shown in FIG. 4, the return in the circuit takes place by a common reference potential (ground), which results due to the resulting long return paths in the event of structural changes in different device classes in differing and unclear conditions relating to the power characteristic, requiring a necessary complex adjustment in each instance.

Figure 5:
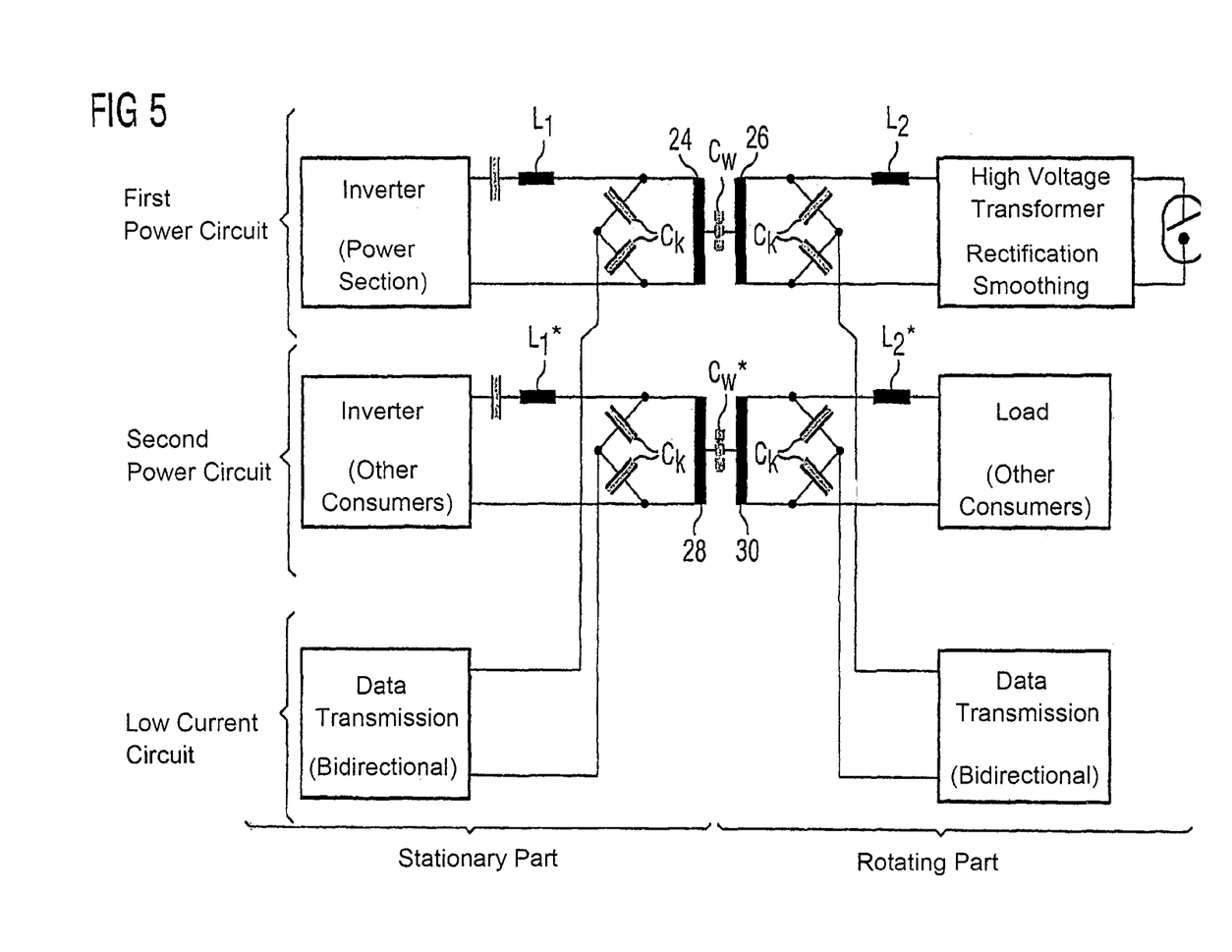
FIG. 5 shows one embodiment of an electric circuit for capacitive data transmission when using two transmitters for the contactless transfer of electric power in a CT device.

In one embodiment, as shown in FIG. 5, two power-circuits (differently designed) and two transmitters are used for capacitive data transmission. A first power-current circuit is for the high-voltage at the x-ray tube (approx. 80 kWatt) and a second power-current circuit is for other supply voltages (10 kWatt).

Figure 2B:
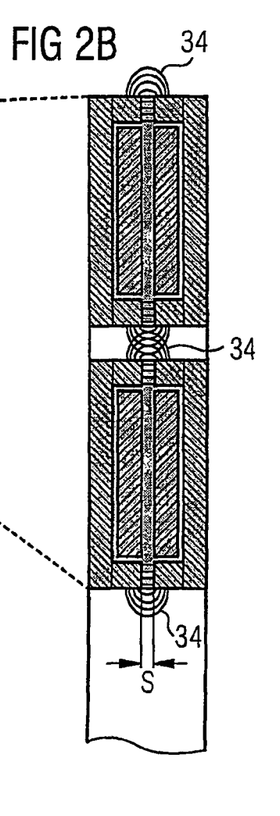
FIG. 2B illustrates the magnetic fields with two transmitters provided.

According to one embodiment, the light-current circuit for the data transmission is distributed to both power-current circuits in such a manner that the data signal transmission is forwarded by way of one transmitter and returned by way of the other transmitter. This results in a closed power circuit by way of the two winding capacitances $C_W$ and $C_W^*$ of both transmitters, resulting in a precisely defined transmission path having reproducible power characteristics.

Where there are a number of (at least two) transmitters on the gantry, for example, one for the x-ray tube voltage and one for the other voltage supplies, the magnetic stray fields 34 of each transmitter influence the respectively adjacent transmitter or the capacitive link. As shown in FIG. 2B, additional transmitters or capacitive links are possible for the described data transmission between the stationary and rotating parts of the gantry.

Figure 2C:
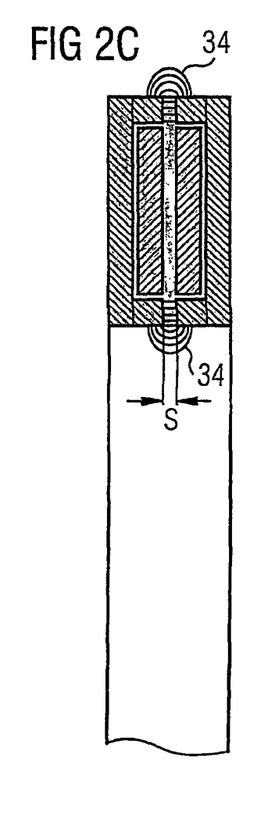
FIG. 2C illustrates the magnetic fields with one transmitter provided.

As shown in FIGS. 2B and 2C by magnetic field lines, the magnetic stray field 34 of a transmitter forms around the air gap marked S between the stationary and rotating parts, which is essential for structural reasons. The larger the air gap, the bigger the magnetic stray field 34.

In one embodiment, the distance between the adjacent transmitters is increased to at least 10 cm with an air gap of S=1 to 2 mm.

The magnetic field lines, in a purely magnetostatic screening (for example using ferrite rings), differ through the always necessary air gap and also outside it.

Figure 6A:
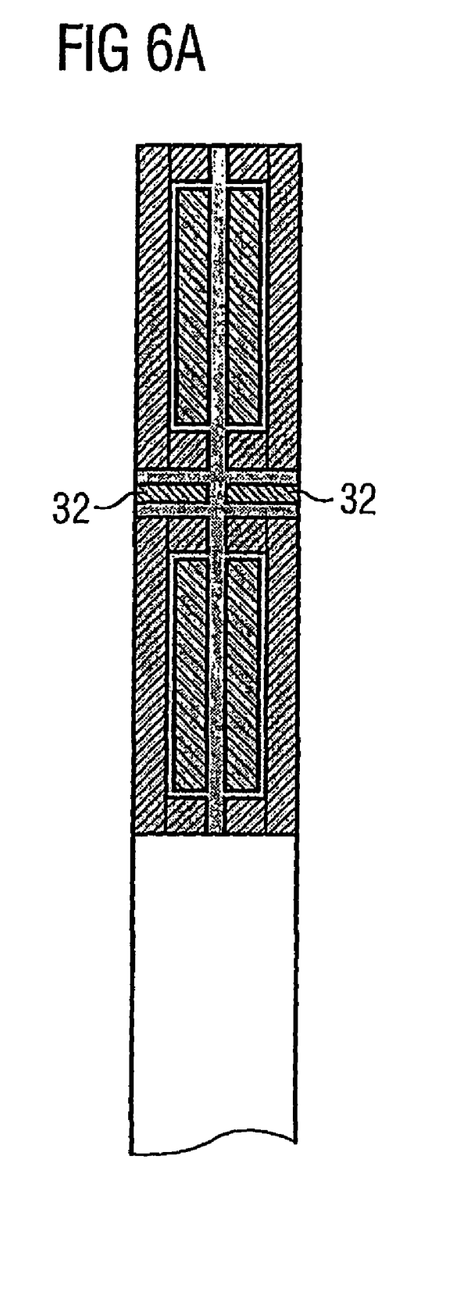
FIG. 6A is a cross sectional view of one embodiment of two transmitters with screening rings and FIG. 6B is a cross sectional view of one embodiment of two transmitters with screening rings disposed in an overlapping manner.

As shown in FIG. 6A, the magnetic scatter fields with contactless transmission of electric power incorporate eddy current dampers using screening rings 32. The current field 34 induces eddy currents in the screening rings, which in turn generate an "opposing field," counter to the original stray field 34. The original stray field 34 is compensated by the opposing field of the screening ring 32. Any material with good electrical conductivity can be used for the screening rings. In one embodiment, screening rings includes iron, which can improve the screening effect due to its high permeability ($\mu_{iron} \geq 1000$).

Figure 6B:
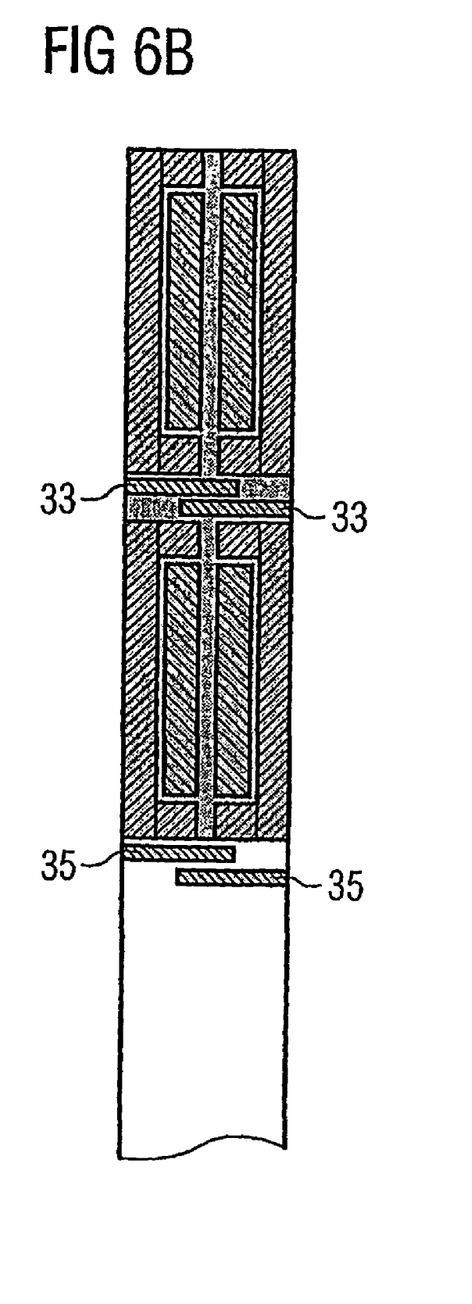

As shown in FIG. 6B, the screening rings 33 are disposed or configured in an overlapping manner so that the screening effect is improved.

The screening rings 35 can be implemented on the opening side, which will keep the stray fields away from the region in which the patient and sensitive electric circuits are located (opening 23).

In one embodiment, further screening rings are attached above the two transmitters. For example, screening rings are attached at the interface with the outside.

The metal supports, on which the transmitters are mounted (for example in the form of an aluminum ring), can also act as eddy current screens. Metal supports having a largely closed area can also protect the electronic systems.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A computed tomography device comprising:
a rotating part having an x-ray tube that is operable to irradiate an object to be examined with x-ray radiation and a detector that is operable to detect the x-ray radiation transmitted through the object; and
a stationary part with a data processing facility that is operable to evaluate the detected x-ray radiation and first and second transmitters that are operable to supply voltage to the rotating part by a contactless transmission of electric power between the stationary part and rotating part,
wherein the first and second transmitters are operable to transmit a contactless data transmission between the stationary and rotating parts, and
wherein screening rings are disposed between the first and second transmitters.

2. The computed tomography device as claimed in claim 1, wherein the contactless data transmission includes an inductive transmission.

3. The computed tomography device as claimed in claim 2, further comprising an electric circuit for the inductive transmission, the electric circuit comprising:
a power circuit comprising the first transmitter and a combination of inductors; and
a data transmission circuit including coupling capacitors.

4. The computed tomography device as claimed in claim 1, wherein the contactless data transmission includes a capacitive transmission.

5. The computed tomography device as claimed in claim 4, further comprising an electric circuit for the conductive transmission, the electric circuit comprising:
- a power circuit comprising the first transmitter;
- a data transmission circuit including coupling capacitors and a common reference potential in a return, the coupling capacitors symmetrically coupling a data signal into the first power circuit.

6. The computed tomography device as claimed in claim 4, wherein the screening rings overlap each other.

7. The computed tomography device as claimed in claim 4, wherein the screening rings are disposed on an opening side, outside the screening rings, or the combination thereof.

8. The computed tomography device as claimed in claim 4, wherein the screening rings comprise an electrically conductive material.

9. The computed tomography device as claimed in claim 4, wherein the first transmitter is operable to forward a data signal and the second transmitter is operable to return the data signal.

10. The computed tomography device as claimed in claim 1, wherein the screening rings overlap each other.

11. The computed tomography device as claimed in claim 1, wherein the screening rings are disposed on an opening side, outside the screening rings, or the combination thereof.

12. The computed tomography device as claimed in claim 1, wherein the screening rings comprise an electrically conductive material.

13. The computed tomography device as claimed in claim 1, wherein the first transmitter is operable to forward a data signal and the second transmitter is operable to return the data signal.

* * * * *